United States Patent
Haramoto et al.

(10) Patent No.: US 9,645,113 B2
(45) Date of Patent: May 9, 2017

(54) IONIZED GAS DETECTOR AND IONIZED GAS DETECTING METHOD

(71) Applicant: TOKYO METROPOLITAN INDUSTRIAL TECHNOLOGY RESEARCH INSTITUTE, Tokyo (JP)

(72) Inventors: Yoshiaki Haramoto, Tokyo (JP); Yasuyuki Hirano, Tokyo (JP); Hiromichi Yoshida, Tokyo (JP)

(73) Assignee: TOKYO METROPOLITAN INDUSTRIAL TECHNOLOGY RESEARCH INSTITUTE, Tokyo (JP)

( * ) Notice: Subject to any disclaimer, the term of this patent is extended or adjusted under 35 U.S.C. 154(b) by 322 days.

(21) Appl. No.: 14/216,588

(22) Filed: Mar. 17, 2014

(65) Prior Publication Data
US 2014/0266231 A1    Sep. 18, 2014

Related U.S. Application Data

(63) Continuation of application No. PCT/JP2012/004025, filed on Jun. 21, 2012.

(30) Foreign Application Priority Data

Sep. 15, 2011   (JP) .................................. 2011-201762

(51) Int. Cl.
*G01N 27/64* (2006.01)
*G01N 27/62* (2006.01)
(Continued)

(52) U.S. Cl.
CPC .............. *G01N 27/64* (2013.01); *G01L 21/30* (2013.01); *G01N 27/62* (2013.01); *G01N 27/70* (2013.01); *G08B 17/11* (2013.01)

(58) Field of Classification Search
CPC ......... G01L 21/30; G01N 27/62; H01J 41/00; G08B 17/11
See application file for complete search history.

(56) References Cited

U.S. PATENT DOCUMENTS

| | | | | |
|---|---|---|---|---|
| 5,530,244 A | * | 6/1996 | Sriram | H01J 49/288 250/281 |
| 6,353,324 B1 | * | 3/2002 | Uber, III | G01R 19/2509 324/457 |
| 2008/0094079 A1 | * | 4/2008 | Suzuki | G01N 27/407 324/713 |

FOREIGN PATENT DOCUMENTS

| | | |
|---|---|---|
| CA | 2075034 A1 | 6/1992 |
| JP | 3-004161 A | 1/1991 |

(Continued)

OTHER PUBLICATIONS

Extended European Search Report for PCT/JP2012004025 mailed May 18, 2015 (6 pages).

(Continued)

*Primary Examiner* — David Gray
*Assistant Examiner* — Michael Harrison
(74) *Attorney, Agent, or Firm* — Osha Liang LLP (57) ABSTRACT

An ionized gas detector includes at least a pair of ion detecting electrodes that detect ions of the ionized measuring-subject gas, an electrode-voltage applying unit that applies a given voltage to the ion detecting electrodes, the electrode-voltage applying unit being configured to be capable of reversing its voltage polarity, a charge amplifier circuit having a charge capacitor that accumulates electric charges generated by voltage application by the electrode-voltage applying unit, an ion current calculating unit that calculates the value of an ion current of ions of the measuring-subject gas, based on a time-dependent change of the volume of electric charges accumulated in the charge capaci- (Continued)

tor of the charge amplifier circuit, and a concentration determining unit that determines the concentration of the measuring-subject gas, based on an ion current value calculated by the ion current calculating unit.

3 Claims, 9 Drawing Sheets

(51) Int. Cl.
  *G01L 21/30* (2006.01)
  *G01N 27/70* (2006.01)
  *G08B 17/11* (2006.01)

(56) References Cited

FOREIGN PATENT DOCUMENTS

| | | |
|---|---|---|
| JP | H03-111998 A | 5/1991 |
| JP | 2010-025795 A | 2/2010 |
| JP | 2010-256165 A | 11/2010 |

OTHER PUBLICATIONS

International Search Report for PCT/JP2012/004025, mailed Jul. 24, 2012 (3 pages).
Written Opinion for PCT/JP2012/004025, mailed Jul. 24, 2012 (7 pages).

\* cited by examiner

1. REVERSAL OF VOLTAGE
2. RUSHING MIGRATION OF ELECTRIC CHARGES
3. CHANGE IN OUTPUT VOLTAGE

FIG. 8 (b)

OUTPUT WAVEFORM

INPUT WAVEFORM OF VOLTAGE BETWEEN ELECTRODES

TIME

REVERSAL OF VOLTAGE

FIG.9 (a)

COMPENSATE LOSS OF ELECTRIC CHARGES

FIG.9 (b)

REVERSAL OF VOLTAGE

FIG. 12

IONIZED GAS DETECTOR AND IONIZED GAS DETECTING METHOD

CROSS-REFERENCE TO RELATED APPLICATIONS

The present application is a continuation application of and, thereby, claims benefit under 35 U.S.C. §120 to a national stage application of PCT Application No. PCT/JP2012/004025, filed on Jun. 21, 2012, which claims priority to Japanese Patent Application No. 2011-201762 filed on Sep. 15, 2011. The contents of the priority applications are incorporated by reference in their entirety.

TECHNICAL FIELD

The present invention relates to an ionized gas detector and an ionized gas detecting method that detect an ionized measuring-subject gas, and particularly relates to an ionized gas detector which includes a charge amplifier circuit having a capacitor, causes the capacitor to accumulate electric charges, and determines the concentration of a measuring-subject gas based on a time-dependent variation of the volume of accumulated electric charges and to an ionized gas detecting method.

BACKGROUND ART

A photo ionization detector (hereinafter "PID") is known as a conventional device for measuring the concentration of a measuring-subject gas. The PID carried out its measurement in the following manner. The measuring-subject gas is led to a pair of voltage applying electrodes inside the PID, where ultraviolet with a short wavelength is emitted onto the gas to ionize it. Ions of the gas are then captured by the voltage applying electrodes and a detection current correlated with the gas concentration is measured. The measured current value is then converted into a gas concentration value. In this manner, the PID measures the concentration of a volatile organic substance, etc.

Figure 10:
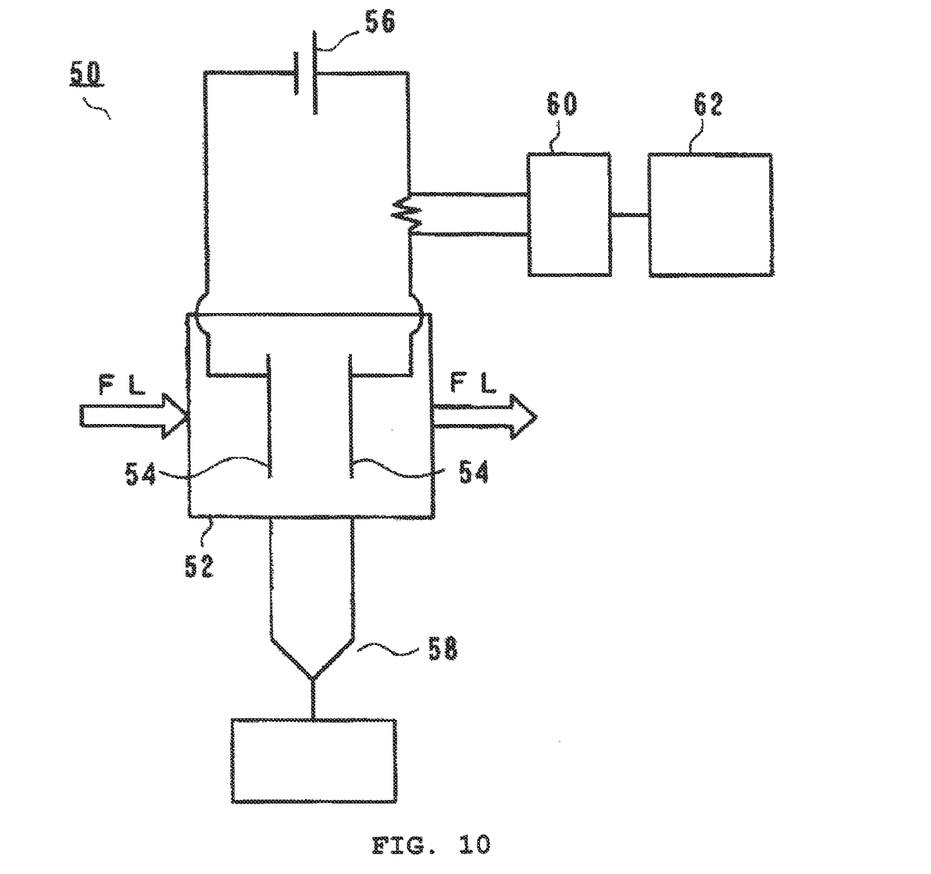
FIG. 10 is a diagrammatic view of an example of a conventional PID.

A PID 50 shown in FIG. 10 includes a detection chamber 52 to and from which a measuring-subject gas is led and discharged, a pair of electrodes 54 disposed in the detection chamber 52, a voltage applying circuit 56 that applies a DC voltage to the electrodes 54, a UV lamp unit 58 that emits ultraviolet onto the measuring-subject fluid (FL) (measuring-subject gas) inside the detection chamber 54, a measuring circuit 60 that measures a current flowing through the electrodes 54, and a computing device 62 that carries out computation for converting a current value into the concentration value of the measuring-subject gas.

According to the PID 50 as a conventional PID, the measuring-subject gas is led into the detection chamber 52, is exposed to the ultraviolet from the UV lamp unit 58, and is discharged from the detection chamber 52. The measuring-subject gas led into the detection chamber 52 is ionized by the ultraviolet from the UV lamp unit 58 disposed on the side wall of the detection chamber 52, and ions or electrons making up the ionized gas are attracted to and captured by the electrodes 54 supplied with the DC voltage inside the detection chamber 52. Hence a current is generated in the circuit connected to the electrodes 54.

The measuring circuit 60 measures the generated current, and the computing device 62 multiplies the measured current value by a factor specified for each substance (substance making up the measuring-subject gas) to calculate the concentration of the measuring-subject gas. Such a PID is sensitive to many kinds of measuring-subject gases and therefore is an effective means for measuring a measuring-subject gas. Being constructed into a compact form, the PID allows easy measurement of a measuring-subject gas and is appreciated as an extremely useful device.

However, because the current flows in a fixed direction in the above conventional PID, a contamination material, such as an insulting material, is deposited on the metal surface of one of the two electrodes supplied with a DC voltage during a long period of service. This contamination prevents the ionized measuring-subject gas from reaching the electrodes, thus preventing the generation of a current flow. As a result, measuring an accurate current value becomes impossible, which means a drop in the PID's sensitivity to the measuring-subject gas. It has been pointed out as a problem that when the metal electrode is covered with the contamination material, the PID loses its measurement sensitivity and becomes incapable of exerting its functions.

For example, patent document 1 discloses a photoionization detector for detecting a volatile organic compound, which detector includes detecting electrodes that detect a volatile organic compound in a measuring-subject fluid, a voltage/current applying unit that applies an AC voltage or alternating current to the detecting electrodes, a UV lamp that emits ultraviolet onto the measuring-subject fluid to ionize the volatile organic compound in the measuring-subject fluid, an exciting circuit that excites the UV lamp, and a measuring unit that measures a current or voltage flowing through or applied across the detecting electrodes.

According to this photoionization detector, an AC voltage or alternating current is applied to the detecting electrodes. For this reason, in addition to an ion current generated at the electrodes, a different current is also generated as the detecting electrodes work as a capacitor. The ionized volatile organic compound changes the dielectric loss of the detecting electrodes, which results in a change in the volume of electric charges accumulated in the capacitor. Hence a change in a current value caused by a change in the volume of electric charges can be measured. Therefore, even if a contamination material is deposited on the detecting electrodes, applying an alternating current to the electrodes prevents the loss of the measurement sensitivity. When an AC voltage or alternating current is applied to two detecting electrodes, even if a contamination material is deposited on one detecting electrode, the other electrode can capture the ionized volatile organic compound. This prevents a drop in the measurement sensitivity.

PRIOR ART DOCUMENTS

Patent Documents

Patent document 1: Japanese Laid-Open Patent Publication No. 2010-256165

SUMMARY OF THE INVENTION

Problems to be Solved by the Invention

The conventional PID detects a measuring-subject gas by a DC voltage applying method. According to this method, electrodes are disposed in anionic atmosphere in which a voltage is applied across the electrodes to generate an ion current, which is to be detected. Because the ion current flowing between the electrodes is usually minute, the minute current is amplified through a DC amplifying circuit so that the amplified current is measured. In this process, however, a drift phenomenon inside the amplifying circuit often affects ion current measurement.

The PID using the DC voltage applying method captures ions by the electrodes. This means that an ionized gas comes in direct contact with the electrodes, which raises a possibility that the electrodes are corroded or covered with a contamination material deposited thereon. Such a situation leads to a problem that the electrodes' sensitivity to the ion current flowing between the electrodes deteriorates.

The technique disclosed by patent document 1 features a method of generating an AC electric field between electrodes. This method allows detection of an ion current flowing between the electrodes even if the electrodes are insulated, thus offering an advantage of measurement not affected by the contaminated or corroded electrodes. However, if a parasitic capacitance between the electrodes is large, a current resulting from the parasitic capacitance between the electrodes turns out to be larger than the minute ion current. This brings difficulty in detecting the ion current, leading to less measurement sensitivity. Besides, detecting the minute ion current requires a device for synchronous detection, etc., which leads to an increase in the size of the detector.

The present invention was conceived in order to solve the above problems, and it is therefore the object of the invention to provide an ionized gas detector and an ionized gas detecting method that measure an ion current for positive and negative ions by detecting the ion current in a simple structure, thereby determine the concentration of a measuring-subject gas, the detector and method not receiving the effect of DC drift caused by a DC voltage applying method, not losing detection sensitivity even if electrodes are contaminated (even if insulated electrodes are used), and being capable of canceling the effect of a parasitic capacitance between the electrodes.

Means for Solving the Problems

To solve the above problems, the present invention provides the following technical means.

According to claim 1 of the present invention, an ionized gas detector includes at least a pair of ion detecting electrodes that detect ions of an ionized measuring-subject gas; an electrode-voltage applying unit that applies a given voltage to the ion detecting electrodes, the electrode-voltage applying unit being configured to be capable of reversing its voltage polarity; a charge amplifier circuit having a charge capacitor that accumulates electric charges generated by voltage application by the electrode-voltage applying unit; anion current calculating unit that calculates the value of an ion current of ions of the measuring-subject gas, based on a time-dependent change of the volume of electric charges accumulated in the charge capacitor of the charge amplifier circuit; a concentration determining unit that determines the concentration of the measuring-subject gas, based on the ion current value calculated by the ion current calculating unit; and a voltage polarity control unit that reverses the polarity of the electrode-voltage applying unit according to the volume of electric charges accumulated in the charge capacitor of the charge amplifier circuit.

According to claim 2 of the present invention, the ionized gas detector of claim 1 includes a circuit connected between the ion detecting electrodes and the input side of the charge amplifier circuit, the circuit having a voltage applying unit different in voltage polarity from the electrode-voltage applying unit configured to be capable of reversing its voltage polarity and an electric charge accumulating unit that accumulates electric charges generated by voltage application by the voltage applying unit; and a voltage polarity reversing unit that when the voltage polarity control unit reverses the polarity of the electrode-voltage applying unit, reverses the voltage polarity of the voltage applying unit, thereby causes the charge accumulating unit to discharge electric charges accumulated therein toward the ion detecting electrodes. According to claim 3 of the present invention, in the ionized gas detector of claim 1, the ion detecting electrodes are covered with an insulating material. According to claim 4 of the present invention, in the ionized gas detector of claim 2, the ion detecting electrodes are covered with an insulating material.

According to claim 5 of the present invention, an ionized gas detecting method includes an ion detecting step of detecting ions of an ionized measuring-subject gas by ion detecting electrodes to which a given voltage is applied; a charge accumulating step of accumulating electric charges generated by ions detected by the ion detecting electrodes; an ion current value calculating step of calculating the value of an ion current of ions of the measuring-subject gas, based on a time-dependent change of the volume of accumulated electric charges; a concentration determining step of determining the concentration of the measuring-subject gas, based on the ion current value calculated at the ion current value calculating step; and a voltage polarity reversing step of reversing the polarity of a voltage applied to the ion detecting electrodes, according to the volume of electric charges accumulated at the charge accumulating step.

According to claim 6 of the present invention, the ionized gas detecting method of claim 5 includes a preliminary charge accumulating step of preliminarily accumulating electric charges generated by application of a voltage different in polarity from a voltage applied to the ion detecting electrodes; and a discharging step of discharging electric charges accumulated at the preliminary charge accumulating step toward the ion detecting electrodes when the polarity of the voltage applied to the ion detecting electrodes is reversed at the voltage polarity reversing step.

Effect of the Invention

Compared to the DC voltage applying detection method, the ionized gas detector and the ionized gas detecting method of the present invention are more advantageous in that they are less affected by DC drift, such as temperature drift, offer high detection sensitivity even if electrodes are contaminated (even if insulated electrode are used), and allow voltage polarity to be reversed. As a result, according to the ionized gas detector and ionized gas detecting method, measurement of positive ions and negative ions can be carried out consecutively and the effect of a parasitic capacitance between the electrodes can be canceled.

BEST MODE FOR CARRYING OUT THE INVENTION

A first embodiment of an ionized gas detector according to the present invention will hereinafter be described, referring to drawings.

Figure 1:
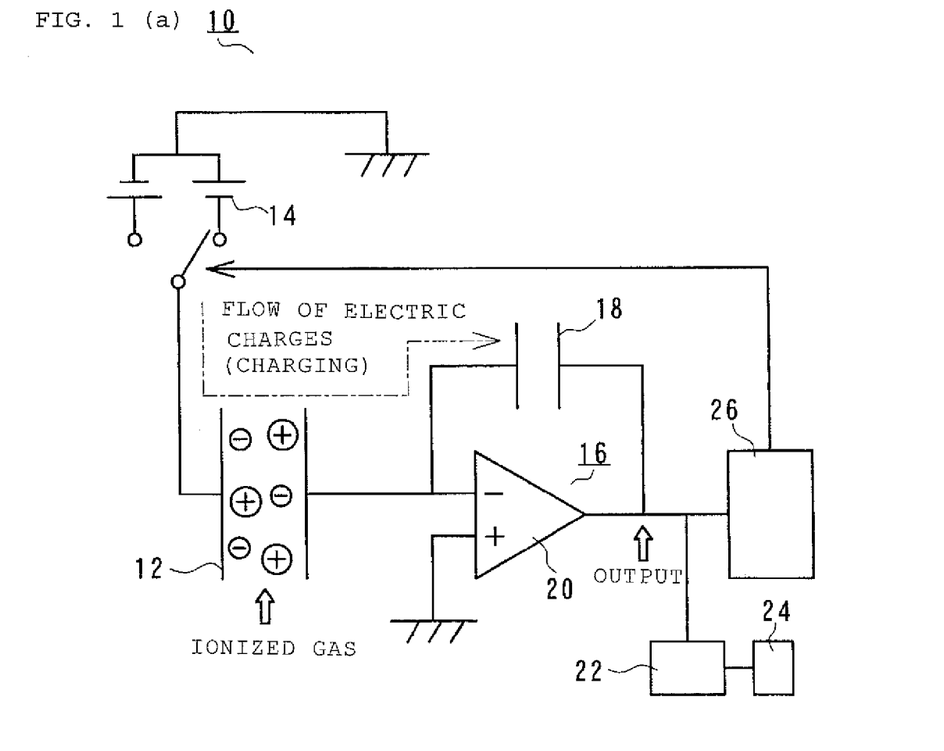
FIG. 1 depicts an example of a first embodiment of an ionized gas detector according to the present invention, including FIG. 1A showing a diagram of an example of a circuit configuration of the detector and FIG. 1B showing a diagram of an example of the relation between a voltage between electrodes and an output voltage from a charge amplifier circuit.
Figure 2:
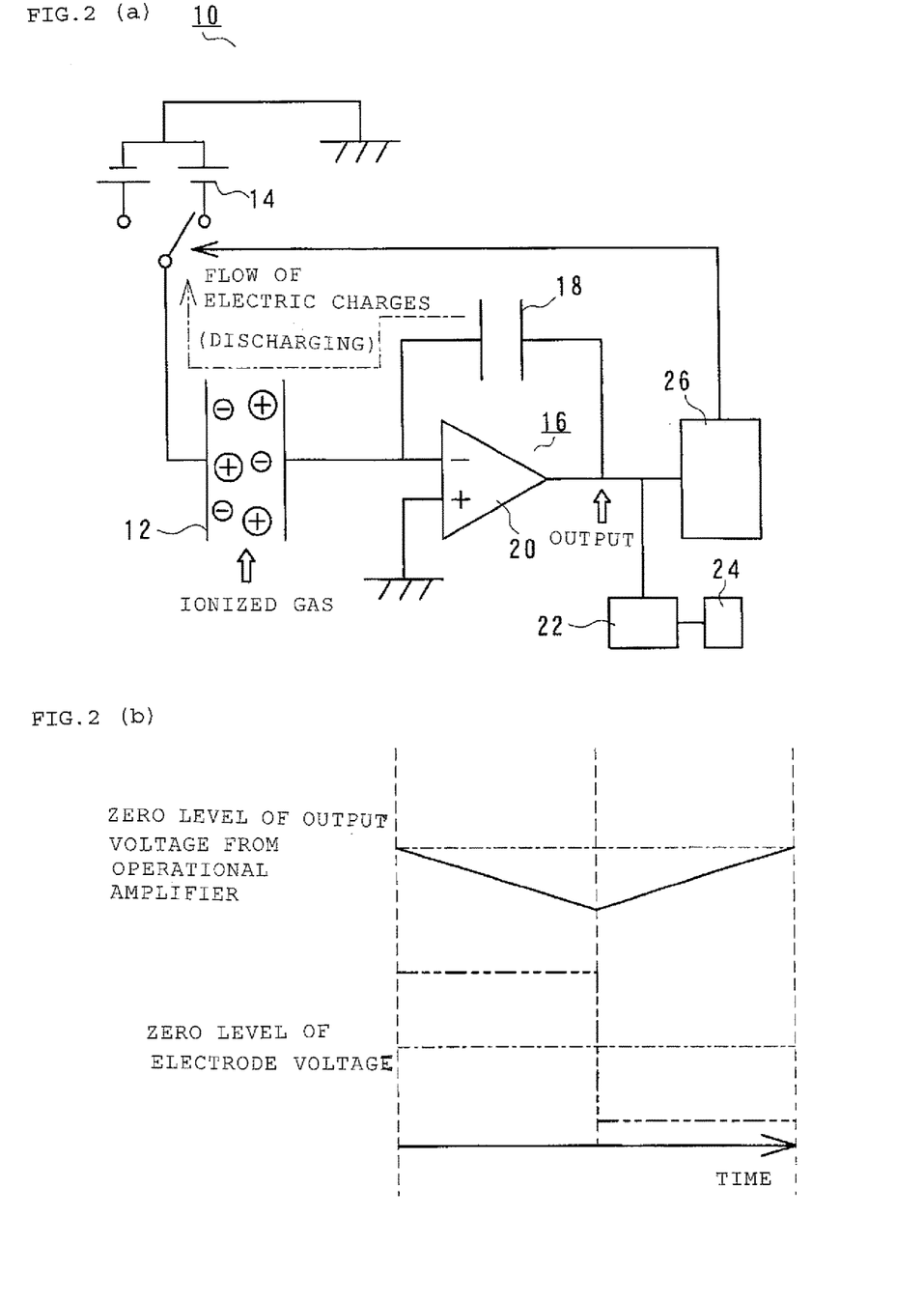
FIG. 2 depicts an example of the first embodiment of the ionized gas detector according to the present invention, including FIG. 2A showing a diagram of an example of a circuit configuration of the detector in which voltage polarity indicated in FIG. 1 is reversed and FIG. 2B showing a diagram of an example of the relation between a voltage between the electrodes and an output voltage from the charge amplifier circuit before and after the reversal of the voltage polarity.

FIG. 1 depicts an example of a configuration of the ionized gas detector according to the first embodiment of the present invention, including FIG. 1A showing a diagram of an example of a circuit configuration of the detector and FIG. 1B showing the relation between a voltage between electrodes and an output voltage from a charge amplifier circuit. FIG. 2 depicts an example of the first embodiment of the ionized gas detector according to the present invention, including FIG. 2A showing a diagram of an example of a circuit configuration of the detector in which voltage polarity indicated in FIG. 1 is reversed and FIG. 2B showing the relation between a voltage between the electrodes and an output voltage from the charge amplifier circuit before and after the reversal of the voltage polarity. In FIG. 1, 10 denotes the ionized gas detector, 12 denotes the ion detecting electrodes, 14 denotes an electrode-voltage applying unit, 16 denotes the charge amplifier circuit, 18 denotes a charge capacitor, 20 denotes an operational amplifier, 22 denotes an ion current calculating unit, 24 denotes a concentration calculating unit, and 26 denotes a voltage polarity control unit.

As shown in FIG. 1A, the ionized gas detector 10 includes the ion detecting electrodes 12 that detect ions of an ionized measuring-subject gas flowing into the ionized gas detector 10, the electrode-voltage applying unit 14 that applies a voltage to the ion detecting electrodes 12 and that is configured to be capable of reversing its voltage polarity. The ionized gas detector 10 also includes the charge amplifier circuit 16 having the charge capacitor 18 that accumulates electric charges generated by voltage application to the ion detecting electrodes 12 and the operational amplifier 20. The ion detecting electrodes 12 may be covered with an insulating material.

The ionized gas detector 10 further includes the voltage polarity control unit 26 that reverses the voltage polarity of the electrode-voltage applying unit 14 according to the volume of electric charges accumulated in the charge capacitor 18, an ion current calculating unit 22 that calculates the value of an ion current, based on a time-dependent change of the volume of electric charges accumulated in the charge capacitor 18 (time-dependent change of the value of an output voltage from the operational amplifier 20), and a concentration determining unit 24 that determines the concentration of the measuring-subject gas, based on the calculated ion current value.

A process of detecting an ionized measuring-subject gas will then be described. Ions of the ionized measuring-subject gas are captured by the ion detecting electrodes 12 to which a given voltage is applied by the electrode-voltage applying unit 14. When the ions are captured by the ion detecting electrodes 12, a current is generated at the ion detecting electrodes 12. As a result, electric charges are accumulated in the charge capacitor 18 of the charge amplifier circuit 16.

As shown in FIG. 1B, as electric charges are accumulated in the charge capacitor 18, an output voltage from the operational amplifier 20 gradually decreases. It is preferable that an operational amplifier with a small bias current (about several hundreds fA), such as CMOS operational amplifier, be used as the operational amplifier 20.

If the charge capacitor 18 with a small capacitance is used, a large output voltage results from a minute ion current. For example, when a voltage V between the electrodes is 100 (V), ion resistance R between the electrodes is 10 G ($\Omega$), and the capacitance C of the charge capacitor 18 is 100 (pF), an output voltage value is calculated by the following equation.

$i = V/R = 100/10G = 10$ nA $$V_{out} = q/C = i*t/C = 10 \text{ nA}/100 \text{ pF}*t = 100t \text{ [V]} \quad \text{[Equation 1]}$$

According to the above equation, the output voltage value 1 millisecond later the start of electric charge accumulation is calculated at 0.1 V and the same 2 milliseconds later is calculated at 0.2 V. The output voltage value thus changes depending on time passage. In this configuration, the ion current can be detected by a simple method.

When the charge capacitor 18 is kept charged with electric charges from the ion current, the operational amplifier 20 reaches its saturated state. Electric charges accumulated in the charge capacitor 18, therefore, must be released at given timing. Usually, the charge capacitor is provided with switches, etc., on its both ends so as to release electric charges accumulated in the charge capacitor. However, these switches pose a problem that the ion current cannot be measured consecutively.

To deal with this problem, according to this embodiment of the present invention, the polarity of the voltage applied to the ion detecting electrodes 12 is reversed at a point of time at which a certain amount of electric charges are accumulated in the charge capacitor 18. This reversal of the voltage polarity causes the ion current between the ion detecting electrodes 12 to flow in the reverse direction, thus causing the charge capacitor 18 to releases electric charges.

Specifically, the voltage polarity control unit 26 measures the value of an output voltage from the operational amplifier 20 to grasp the volume of electric charges accumulated in the charge capacitor 18, and when the volume of electric charges reaches a given volume, reverses the voltage polarity of the electrode-voltage applying unit 14 through voltage polarity control.

When the voltage polarity control unit 26 reverses the voltage polarity of the electrode-voltage applying unit 14, electric charges accumulated in the charge capacitor 18 are discharged therefrom due to the ionized gas (positive ions) between the electrodes, as shown in FIG. 2A. As a result, the output voltage from the operational amplifier 20 increases gradually from the point of voltage polarity reversal toward a point of zero output voltage level, as shown in FIG. 2B.

Because charges accumulated in the charge capacitor 18 are collected from the ion detecting electrodes 12, a process of collecting positive and negative ions can be controlled by an electric field between the ion detecting electrodes 12 (which means that measurement of positive and negative ions can be carried out consecutively). In addition, by measuring a change in the speed of accumulation of charges in the charge capacitor 18 and in the speed of releasing of charges from the charge capacitor 18, a difference in migration speed between positive ions and negative ions of the ionized measuring-subject gas can be measured.

The ion current calculating unit 22 calculates the value of the ion current based on a time-dependent change of the output voltage from the operational amplifier 20, that is, a time-dependent change of electric charges accumulated in the charge capacitor 18. Specifically, the value of the ion current is calculated by the following equation.

$$i = C\frac{(V_{out2} - V_{out1})}{(t_2 - t_1)} \qquad \text{[Equation 2]}$$

Vout1: An output voltage from the charge amplifier
t1: Time at which Vout1 is measured
Vout2: An output voltage from the charge amplifier
t1: Time at which Vout2 is measured In an ordinary DC amplifying circuit, an offset voltage may change due to temperature drift, etc., and this offset voltage directly affects measurements. Adding drift-caused measurement errors δVout1 and δVout2 to the output voltages Vout1 and Vout2 yields the following equation.

$$i = C\frac{(V_{out2} + \delta V_{out2} - V_{out1} - \delta V_{out1})}{(t_2 - t_1)} \qquad \text{[Equation 3]}$$

However, because a time difference between a point of measurement of Vout1 and a point of measurement of Vout2 is short (1 second at maximum), δVout1 and δVout2 are considered to be equal to each other. Hence the equation 3 turns out to be identical with the equation 2, which indicates the effect of DC drift is eliminated.

Based on the value of the ion current calculated by the ion current calculating unit 22, the concentration determining unit 24 determines the concentration of the measuring-subject gas. The concentration determining unit 24 determines the concentration by, for example, multiplying the value of the ion current by a given factor.

Figure 5:
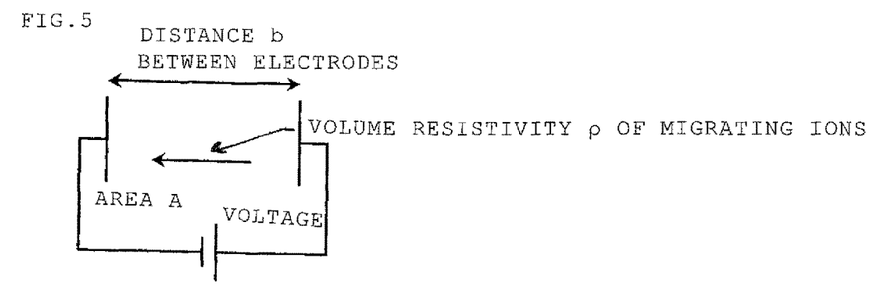
FIG. 5 is a diagram of an example of the relation between an electric field and an ion current in the ion detecting electrodes.

An example of the relation between the electric filed and the ion current between the ion detecting electrodes 12 is shown in FIG. 5. The ion current is defined by the following equation.

$$i = \frac{A}{\rho b}V \qquad \text{[Equation 4]}$$

ρ: Volume resistivity [Ωm] by ions
A: The area [m²] of the electrode
b: The distance [m] between the electrodes If, for example, 50% of the surface of the ion detecting electrodes 12 is contaminated, the area of the electrodes for detecting ions is reduced by 50%, which means the ion current created by the DC electric field is reduced by 50%. A diagrammatic view of an example of the ion detecting electrodes 12 with their surface insulated is shown in FIG. 6.

Figure 6:
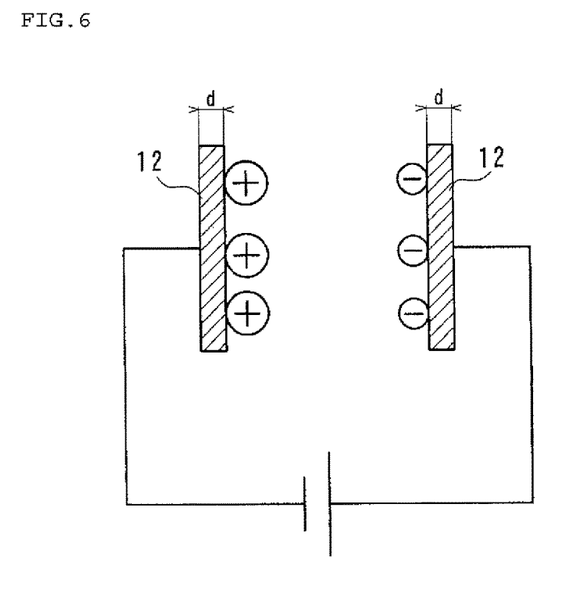
FIG. 6 is a diagrammatical view of an example of the ion detecting electrodes whose surface is insulated.
Figure 7:
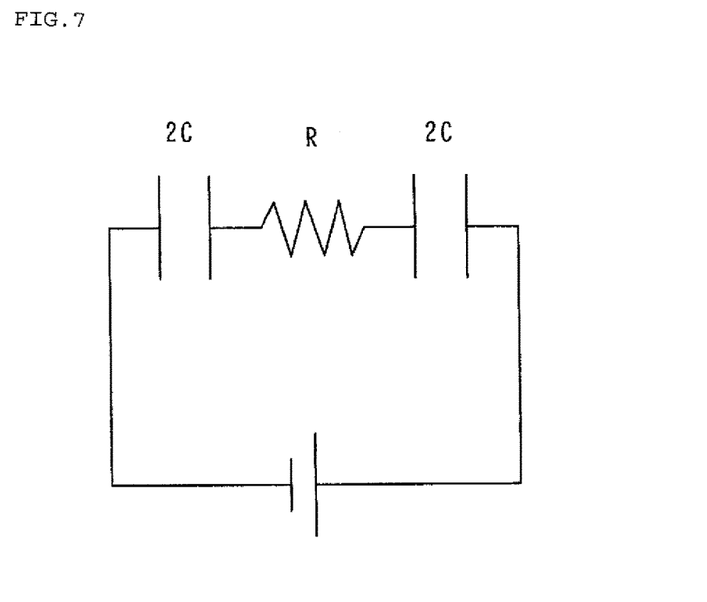
FIG. 7 is a diagram of an example of an equivalent circuit in which the capacitance of each electrode insulated with an insulating film is expressed as 2C and ion migration in an ionic atmosphere is expressed as resistance R.

In a condition indicated in FIG. 6, the surface of each insulating film having a thickness d is charged with ions. As a result, electric charges gather on the surface of the ion detecting electrodes 12. When the capacitance of the electrodes covered with the insulating film is denoted as 2C and the migration of ions in an ionic atmosphere is expressed as resistance R, an equivalent circuit of FIG. 7 is obtained. The relation between voltage and current in this circuit is expressed by the following equation.

$$E = Ri(t) + \frac{1}{C}Q(t) = R\frac{d}{dt}Q(t) + \frac{1}{C}Q(t) \qquad \text{[Equation 5]}$$

$$Q(t) = CE\left(1 - \exp\left(-\frac{1}{RC}t\right)\right)$$

$$i(t) = -\frac{E}{R}\exp\left(-\frac{1}{RC}t\right)$$

Suppose the circuit operates under the following conditions.
The area of the electrode (A): 10 mm×10 mm
Insulating film: polyimide (dielectric constant $\in_r$=4)
Thickness of the insulating film (d): 10 μm
Resistance by ions (R): 10 GΩ
Electrode voltage (E): 100 V
Then, the following equations give a capacitance C, a time constant τ, and an initial current value i for the insulated electrode.

$$C = \varepsilon_0 \varepsilon_r \frac{A}{2d} = 8.85*10^{-12}*4*\frac{(0.01)^2}{2*50*10^{-6}} = 177 \text{ pF} \qquad \text{[Equation 6]}$$

$$\tau = R*C = 10 \text{ GΩ}*177 \text{ pF} = 1.77 \text{ sec}$$

$$i(0) = -\frac{E}{R} = -\frac{100 \text{ V}}{10 \text{ GΩ}} = 10 \text{ nA}$$

A case is assumed where the capacitance of the charge capacitor is set to 100 pF and ionized gas detection is carried out until an output voltage from the charge amplifier reaches 2 V. The output voltage is given by an equation 7. If i(t) in this equation is approximated at 10 nA, an equation 8 results. Hence a variation ratio between a current created by the DC voltage applying method and a current created by electrodes covered with the insulting film is given by an equation 9, Output voltage: $Vout = \dfrac{i(t)t}{C}$ [Equation 7]

$t = \dfrac{2\text{ V} * 100\text{ pF}}{10\text{ nA}} = 20$ msec [Equation 8]

Variation ratio: [Equation 9]

$t = \dfrac{i(t)}{i(0)} = \dfrac{-\dfrac{E}{R}\exp\left(-\dfrac{1}{RC}t\right)}{-\dfrac{E}{R}} = \exp\left(-\dfrac{1}{RC}t\right) = \exp\left(-\dfrac{0.02}{1.77}\right) = 0.988$ Usually, an allowable error of the ionized gas detector is about ±10%. Therefore, the above variation ratio of 0.988 indicates a fact that the effect of the insulated electrodes is extremely tiny. The time constant for the insulated electrodes is expressed by an equation 10. As the time constant becomes larger, a difference between a current created by the method of the first embodiment and a current created by the DC voltage applying method becomes smaller. R depends on the concentration of the ionized gas, and C is determined by the thickness and dielectric constant of the insulating film. While the insulating film is made of polyimide and is 10 μm in thickness, the insulating film may be thicker than this. In such a case, using the insulating film made of a material with a high dielectric constant allows precise measurement of the ionized gas.

$\tau \leq R*C$ [Equation 10]

(Experiment 1)

Figure 3:
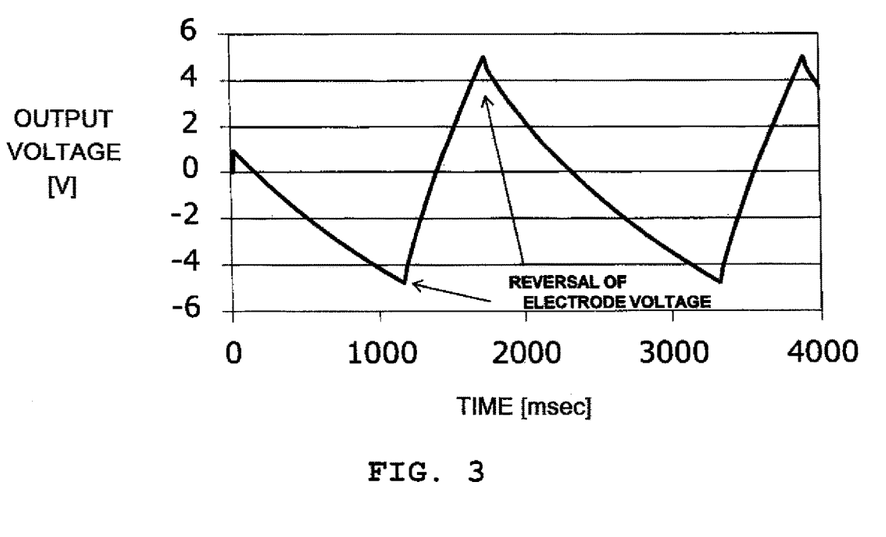
FIG. 3 is a graph indicating the result of an experiment having revealed the relation between an output voltage and time that results when the ionized gas detector of the first embodiment of the present invention detects ionized toluene (10 ppm) that is a volatile organic substance.

An ionized gas detection experiment has been conducted, using the ionized gas detector of the first embodiment of the present invention, under the following measurement conditions. A result of the experiment is shown in FIG. 3.

Ionized gas: toluene 10 ppm
Applied voltage: 20 V
Capacitance: 100 pF
Ion detecting electrodes: Electrodes insulated with a polyimide film As shown in FIG. 3, the reversal of the voltage polarity causes an increase or decrease in an output voltage from the operational amplifier 20. This demonstrates a fact that even if insulated electrodes are used as the ion detecting electrodes, the ionized gas detector of this embodiment can detect an ionized gas with precision equal to the precision of detection of an ionized gas by the DC voltage applying method, thanks to transition phenomenon.

A second embodiment of the ionized gas detector according to the present invention will then be described, referring to drawings.

Figure 4:
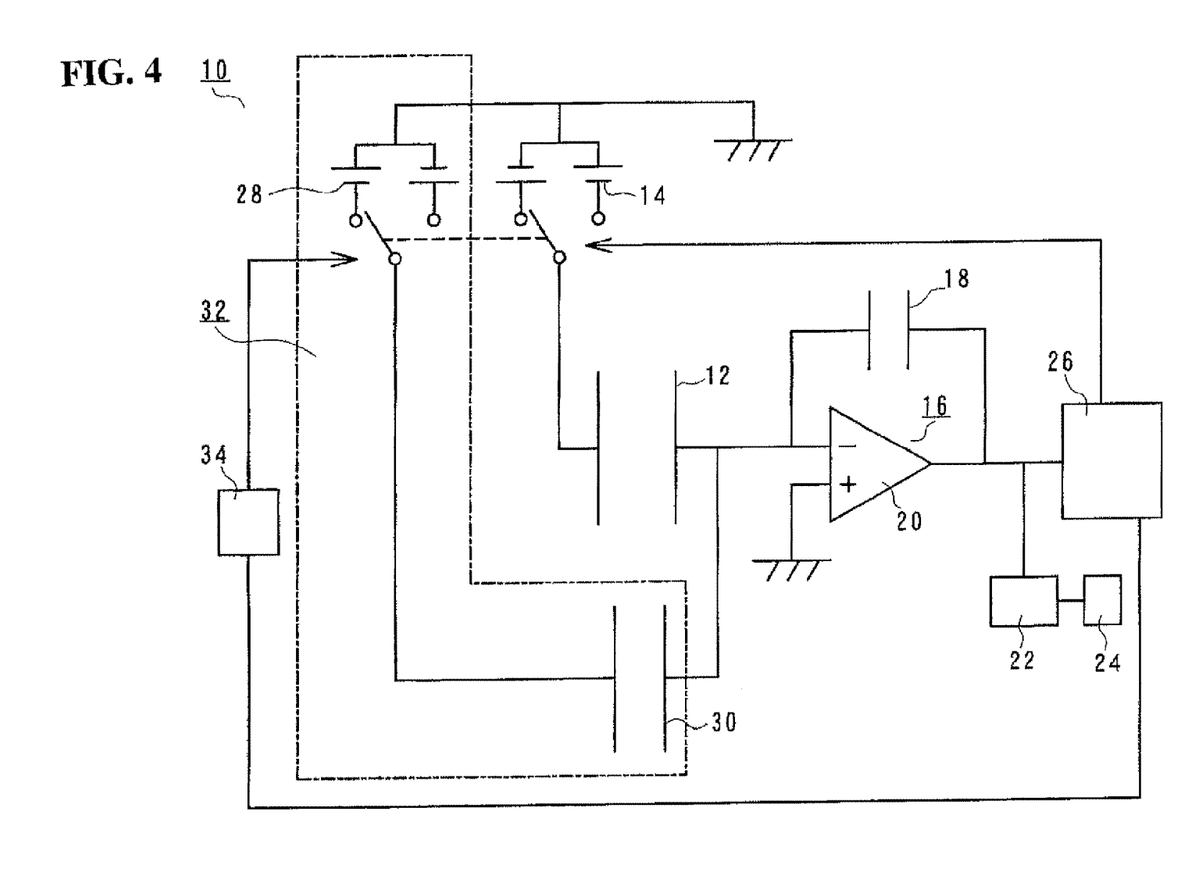
FIG. 4 depicts an example of a second embodiment of the ionized gas detector according to the present invention, showing a diagram of an example of a circuit configuration of the detector.

FIG. 4 depicts an example of a configuration of the ionized gas detector of the second embodiment of the present invention, showing a diagram of an example of a circuit configuration of the detector. In FIG. 4, 28 denotes a voltage applying unit, 30 denotes a charge accumulating unit, 32 denotes a compensating circuit, and 34 denotes a voltage polarity reversing unit. Other components are denoted by the same reference numerals as used in FIGS. 1 and 2.

As shown in FIG. 4, the ionized gas detector 10 includes the ion detecting electrodes 12 that detect ions of an ionized measuring-subject gas flowing into the ionized gas detector 10, the electrode-voltage applying unit 14 that applies a voltage to the ion detecting electrodes 12 and that is configured to be capable of reversing its voltage polarity. The ionized gas detector 10 also includes the charge amplifier circuit 16 having the charge capacitor 18 that accumulates electric charges generated by voltage application to the ion detecting electrodes 12 and the operational amplifier 20. The ion detecting electrodes 12 may be covered with an insulating material.

The ionized gas detector 10 further includes the voltage polarity control unit 26 that reverses the voltage polarity of the electrode-voltage applying unit 14 according to the volume of electric charges accumulated in the charge capacitor 18, the ion current calculating unit 22 that calculates the value of an ion current, based on a time-dependent change of the volume of electric charges accumulated in the charge capacitor 18, and the concentration determining unit 24 that determines the concentration of the measuring-subject gas, based on the calculated ion current value.

The ionized gas detector 10 further includes the compensating circuit 32 connected between the ion detecting electrodes 12 and the input side of the operational amplifier 20, the compensating circuit 32 having the voltage applying unit 28 different in voltage polarity from the electrode-voltage applying unit 14 configured to be capable of reversing its voltage polarity and the electric charge accumulating unit 30 that accumulates electric charges generated by voltage application by the voltage applying unit 28, and the voltage polarity reversing unit 34 that reverses the voltage polarity of the voltage applying unit 28 in synchronization with control of reversal of the voltage polarity of the electrode-voltage applying mean 14 by the voltage polarity control unit 26.

Figure 8:
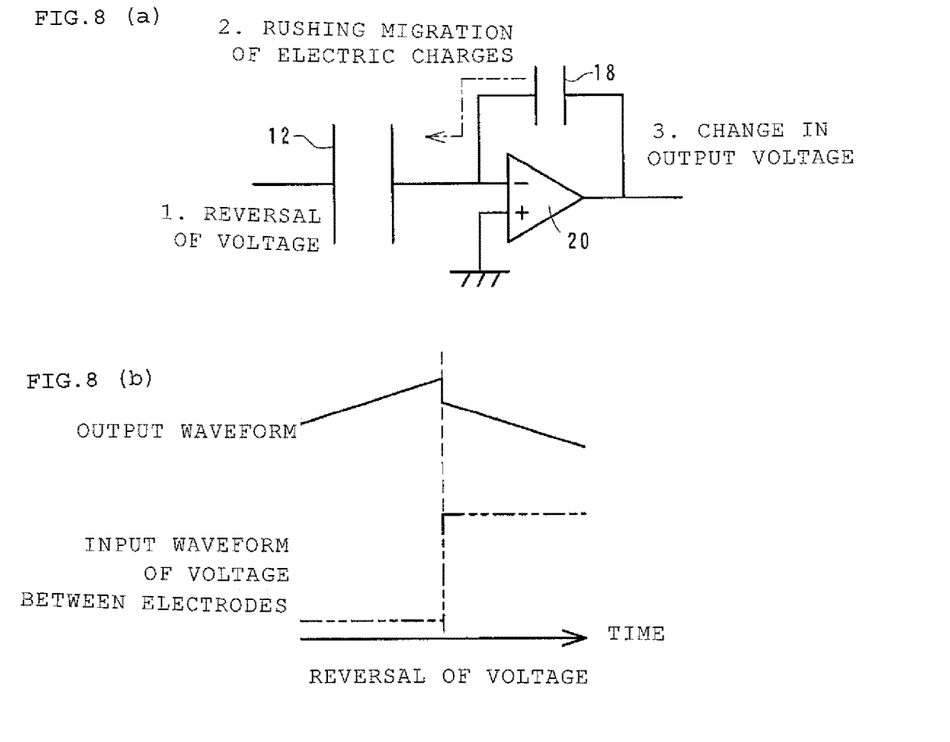
FIG. 8 depicts an example of the relation between the migration of electric charges caused by the reversal of voltage polarity and an output response, including FIG. 8A showing an example of a circuit configuration of the detector and FIG. 8B showing an example of an output response.

When the volume of electric charges accumulated in the charge capacitor 18 grows and reaches a given volume of electric charges, the voltage polarity control unit 26 reverses the voltage polarity of the electrode-voltage applying unit 14. At this point, when a resistant element, etc., is not present between the charge capacitor 18 and the ion detecting electrodes 12, electric charges migrate with a rush from the charge capacitor 18 to the ion detecting electrodes 12. This results in a sharp change of an output voltage from the operational amplifier 20, thus leading to an error in calculation of an ion current value (see FIG. 8).

It is known that such a sharp change of the output voltage occurs conspicuously when a voltage applied to the ion detecting electrodes 12 is raised or a parasitic capacitance between the ion detecting electrodes 12 is large (in a case where the distance between the electrodes is small and the electrode size is large). To improve the precision of detection of the ionized gas, it is necessary to raise the voltage applied to the ion detecting electrodes 12 and reduce the distance between the electrodes, in which case suppressing a sharp change of the output voltage is essential.

In this embodiment, to prevent a sharp change of the volume of electric charges in the charge capacitor 18, the charge accumulating unit 30 (capacitor) of the compensating circuit 32 connected in parallel with the ion detecting electrodes 12 compensates the loss of electric charges. Specifically, the voltage applying unit 28 applies a voltage different in polarity from a voltage applied by the electrode-voltage applying unit 14 to the charge accumulating unit 30, thereby accumulates electric charges in advance in the charge accumulating unit 30. When the voltage polarity reversing unit 34 finds that the voltage polarity control unit 26 has reversed the voltage polarity of the electrode-voltage applying unit 14, the voltage polarity reversing unit 34 reverses the voltage polarity of the voltage applying unit 28.

As a result, electric charges accumulated in the charge accumulating unit 30 migrate toward the ion detecting electrodes 12. These migrating electric charges thus compensate the rushing migration of electric charges from the charge capacitor 18 to the ion detecting electrodes 12. The voltage applied by the voltage applying unit 28 is adjusted to the voltage adequate for compensating the rushing migration of electric charges from the charge capacitor 18 to the ion detecting electrodes 12 or may be automatically adjusted. This further improves the precision of ion current calculation.

When the voltage polarity reversing unit 34 reverses the voltage polarity of the voltage applying unit 28 again, the charge accumulating unit 30 starts accumulating electric charges again. These accumulating electric charges suppress a sharp change of the volume of electric charges in the charge capacitor 18 that occurs when the charge capacitor 18 discharges again (under the alternating influence of positive ions and negative ions).

Figure 9:
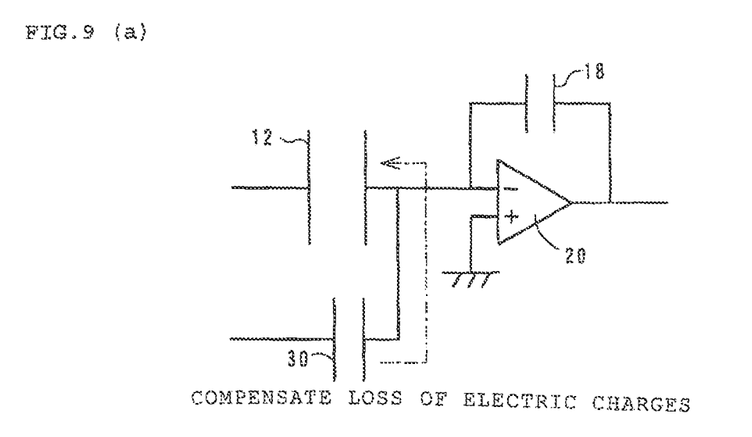
FIG. 9 depicts an example of the relation between the migration of electric charges caused by the reversal of voltage polarity and an output response in a case where the detector is provided with a compensating circuit, including FIG. 9A showing an example of a circuit configuration of the detector and FIG. 9B showing an example of an output response.

In this configuration, as shown in FIG. 9, the output voltage from the operational amplifier 20 can be kept stable even if the voltage polarity is reversed, which means the effect of the parasitic capacitance between the electrodes is canceled.

A process of detecting the ionized measuring-subject gas will then be described. Ions of the ionized measuring-subject gas are captured by the ion detecting electrodes 12 to which a given voltage is applied by the electrode-voltage applying unit 14. When the ions are captured by the ion detecting electrodes 12, a current is generated at the ion detecting electrodes 12. As a result, electric charges are accumulated in the charge capacitor 18 of the charge amplifier circuit 16.

As electric charges are accumulated in the charge capacitor 18, an output voltage from the operational amplifier 20 gradually decreases. It is preferable that an operational amplifier with a small bias current (about several hundreds fA), such as CMOS operational amplifier, be used as the operational amplifier 20. If the charge capacitor 18 with a small capacitance is used, a large output voltage results from a minute ion current.

When the charge capacitor 18 is kept charged with electric charges from the ion current, the operational amplifier 20 reaches its saturated state. Charges accumulated in the charge capacitor 18, therefore, must be released at given timing. Usually, the charge capacitor is provided with switches, etc., on its both ends so as to release electric charges accumulated in the charge capacitor. However, these switches pose a problem that the ion current cannot be measured consecutively.

To deal with this problem, according to this embodiment of the present invention, the polarity of the voltage applied to the ion detecting electrodes 12 is reversed at a point of time at which a certain amount of electric charges are accumulated in the charge capacitor 18. This reversal of the voltage polarity causes the ion current between the ion detecting electrodes 12 to flow in the reverse direction, thus causing the charge capacitor 18 to releases electric charges.

Specifically, the voltage polarity control unit 26 measures the value of an output voltage from the operational amplifier 20 to grasp the volume of electric charges accumulated in the charge capacitor 18, and when the volume of electric charges reaches a given volume, reverses the voltage polarity of the electrode-voltage applying unit 14 through voltage polarity control.

When the voltage polarity control unit 26 reverses the voltage polarity of the electrode-voltage applying unit 14, electric charges accumulated in the charge capacitor 18 are discharged therefrom due to the ionized gas (positive ions) between the electrodes. As a result, the output voltage from the operational amplifier 20 increases gradually from the point of voltage polarity reversal toward a point of zero output voltage level.

Because charges accumulated in the charge capacitor 18 are collected from the ion detecting electrodes 12, a process of collecting positive and negative ions can be controlled by an electric field between the ion detecting electrodes 12. In addition, by measuring a change in the speed of accumulation of charges in the charge capacitor 18 and in the speed of releasing of charges from the charge capacitor 18, a difference in migration speed between positive ions and negative ions can be measured.

When the voltage polarity control unit 26 reverses the voltage polarity of the electrode-voltage applying unit 14, electric charges accumulated in the charge capacitor 18 migrates with a rush toward the ion detecting electrodes 12. To prevent this, the voltage polarity reversing unit 34 reverses the voltage polarity of the voltage applying unit 28 in synchronization with the reversal of the voltage polarity of the electrode-voltage applying unit 14 by the voltage polarity control unit 26.

As a result, electric charges are discharged from the charge accumulating unit 30 (capacitor) of the compensating circuit 32 connected in parallel with the ion detecting electrode 12, the charge accumulating unit 30 accumulating the electric charges in advance because of an applied voltage different in voltage polarity from a voltage applied by the electrode-voltage applying unit 14, to the ion detecting electrodes 12.

Through this voltage polarity control process, the output voltage from the operational amplifier 20 can be kept stable even when the voltage polarity control unit 26 reverses the voltage polarity of the electrode-voltage applying unit 14 (which means the effect of the parasitic capacitance between the electrodes is canceled.) The voltage applied by the voltage applying unit 28 is adjusted to the voltage adequate for compensating the rushing migration of electric charges from the charge capacitor 18 to the ion detecting electrodes 12 or may be automatically adjusted. This further improves the precision of ion current calculation.

(Experiment 2)

The ionized gas detector of the first and second embodiments of the present invention has been subjected to an experiment for measuring a change in an output voltage from the operational amplifier 20 using an oscilloscope. Experiment results are shown in graphs of FIG. 11 (first embodiment) and FIG. 12 (second embodiment).

Figure 11:
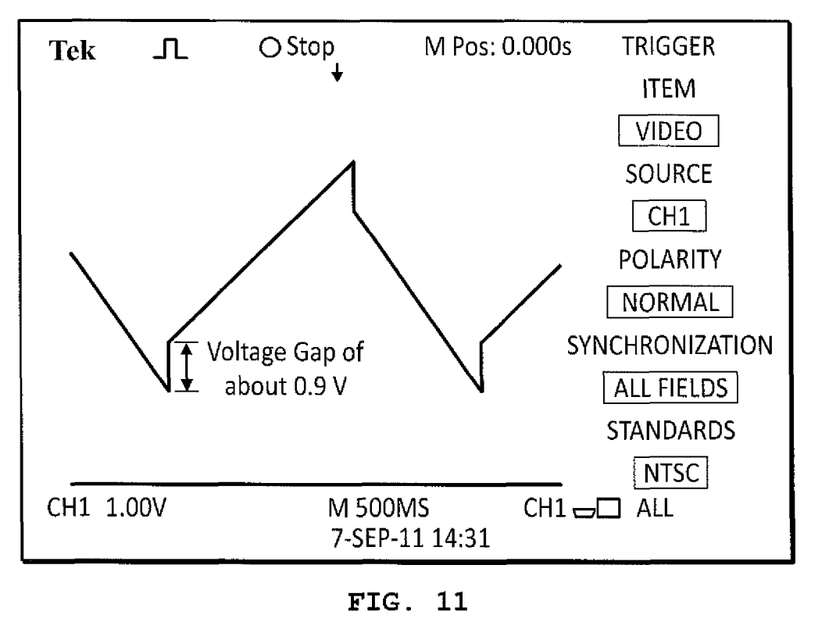
FIG. 11 is a graph indicating the result of an experiment of measuring a change in an output voltage from an operational amplifier of the ionized gas detector of the first embodiment of the present invention, using an oscilloscope.

In the experiment of the ionized gas detector of the first embodiment, a voltage to be applied to the ion detecting electrodes 12 is set to ±35 V and the voltage polarity is reversed three times. FIG. 11 demonstrates that when the voltage polarity is reversed in the ionized gas detector of the first embodiment, electric charges migrate with a rush, creating a voltage gap of 0.9V. This voltage gap is the cause of an error in ion current value calculation.

Figure 12:
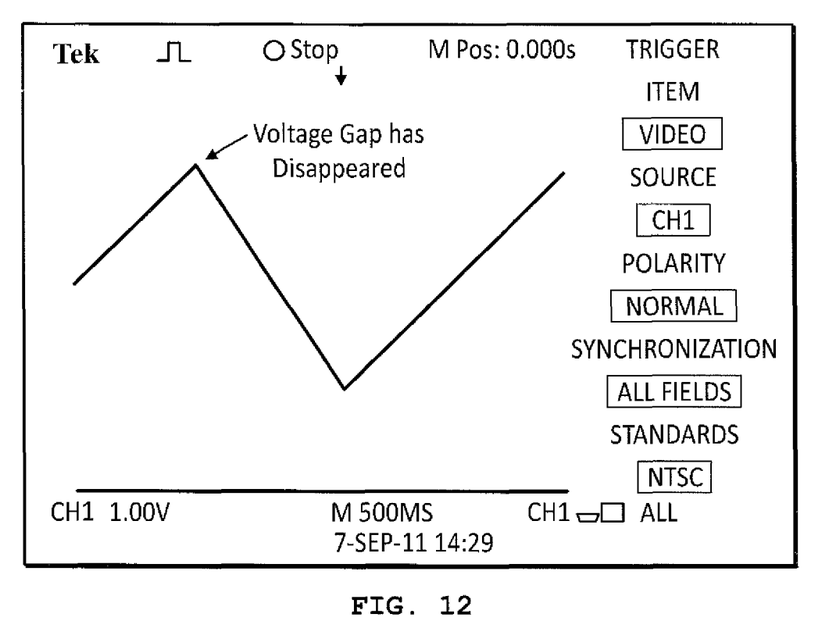
FIG. 12 is a graph indicating the result of an experiment of measuring a change in an output voltage from the operational amplifier of the ionized gas detector of the second embodiment of the present invention, using an oscilloscope.

In the experiment of the ionized gas detector of the second embodiment, a voltage to be applied to the ion detecting electrodes 12 is set to ±35 V and the voltage polarity is reversed twice. A voltage applied by the voltage applying unit 28 is adjusted automatically to a proper voltage so as to prevent the rushing migration of electric charges (to prevent creation of a voltage gap). FIG. 12 demonstrates that in the ionized gas detector of the second embodiment, the rushing migration of electric charges can be suppressed even when the voltage polarity is reversed.

INDUSTRIAL APPLICABILITY

According to the ionized gas detector and the ionized gas detecting method of the present invention, the ionized gas detector configured to be simple and compact can detect an ionized gas at high precision, is less affected by temperature drift, etc., compared to the detector carrying out the DC voltage applying method, and can perform highly precise detection even if the ion detecting electrodes are contaminated. The ionized gas detector and ionized gas detecting method, therefore, are usable for ionized gas detection that needs to be carried out in various situations and environments.

EXPLANATION OF LETTERS AND NUMERALS

10 Ionized gas detector
12 Ion detecting electrode
14 Electrode-voltage applying unit
16 Charge amplifier circuit
18 Charge capacitor
20 Operational amplifier
22 Ion current calculating unit
24 Concentration determining unit
26 Voltage polarity control unit
28 Voltage applying unit
30 Charge accumulating unit
32 Compensating circuit
34 Voltage polarity reversing unit

The invention claimed is:

1. An ionized gas detector comprising;
   at least a pair of ion detecting electrodes that detect ions of an ionized measuring-subject gas;
   an electrode-voltage applying unit that applies a given voltage to the ion detecting electrodes, the electrode-voltage applying unit being configured to be capable of reversing its voltage polarity;
   a charge amplifier circuit having a charge capacitor that accumulates electric charges generated by voltage application by the electrode-voltage applying unit;
   an ion current calculating unit that calculates a value of an ion current of ions of the measuring-subject gas, based on a time-dependent change of a volume of electric charges accumulated in the charge capacitor of the charge amplifier circuit;
   a concentration determining unit that determines concentration of the measuring-subject gas, based on an ion current value calculated by the ion current calculating unit;
   a voltage polarity control unit that reverses polarity of the electrode-voltage applying unit according to a volume of electric charges accumulated in the charge capacitor of the charge amplifier circuit;
   a circuit connected between the ion detecting electrodes and an input side of the charge amplifier circuit, the circuit having a voltage applying unit different in voltage polarity from the electrode-voltage applying unit configured to be capable of reversing its voltage polarity and an electric charge accumulating unit that accumulates electric charges generated by voltage application by the voltage applying unit; and
   a voltage polarity reversing unit that when the voltage polarity control unit reverses polarity of the electrode-voltage applying unit, reverses voltage polarity of the voltage applying unit, thereby causes the charge accumulating unit to discharge electric charges accumulated therein toward the ion detecting electrodes.

2. The ionized gas detector according to claim 1, wherein the ion detecting electrodes are covered with an insulating material.

3. An ionized gas detecting method comprising:
   an ion detecting step of detecting ions of an ionized measuring-subject gas by ion detecting electrodes to which a given voltage is applied;
   a charge accumulating step of accumulating electric charges generated by ions detected by the ion detecting electrodes;
   an ion current value calculating step of calculating a value of an ion current of ions of the measuring-subject gas, based on a time-dependent change of a volume of the accumulated electric charges;
   a concentration determining step of determining concentration of the measuring-subject gas, based on an ion current value calculated at the ion current value calculating step;
   a voltage polarity reversing step of reversing polarity of a voltage applied to the ion detecting electrodes, according to a volume of the electric charges accumulated at the charge accumulating step;
   a preliminary charge accumulating step of preliminarily accumulating electric charges generated by application of a voltage different in polarity from a voltage applied to the ion detecting electrodes; and
   a discharging step of discharging electric charges accumulated at the preliminary charge accumulating step toward the ion detecting electrodes when polarity of the voltage applied to the ion detecting electrodes is reversed at the voltage polarity reversing step.

* * * * *